United States Patent
Linder (10) Patent No.: US 8,821,980 B2
(45) Date of Patent: Sep. 2, 2014

(54) METHOD OF MAKING A PATTERNED LAYER FOR ABSORBENT ARTICLE

(71) Applicant: SCA Hygiene Products AB, Göteborg (SE)

(72) Inventor: Michael Linder, Gothenburg (SE)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 13/716,958

(22) Filed: Dec. 17, 2012

(65) Prior Publication Data
US 2013/0100224 A1    Apr. 25, 2013

Related U.S. Application Data

(63) Continuation of application No. 11/017,659, filed on Dec. 22, 2004, now abandoned.

(60) Provisional application No. 60/531,037, filed on Dec. 22, 2003.

(51) Int. Cl.
| | |
|---|---|
| *A61F 13/15* | (2006.01) |
| *A61F 13/49* | (2006.01) |
| *A61F 13/84* | (2006.01) |
| *B41J 2/005* | (2006.01) |
| *A61F 13/514* | (2006.01) |

(52) U.S. Cl.
CPC .......... *B41J 2/005* (2013.01); *A61F 13/84* (2013.01); *A61F 2013/8497* (2013.01); *A61F 13/514* (2013.01); *A61F 13/49009* (2013.01)
USPC ........... 427/288; 427/256; 427/257; 604/358; 604/385.01; 604/385.21; 604/385.22

(58) Field of Classification Search
None
See application file for complete search history.

(56) References Cited

U.S. PATENT DOCUMENTS

| | | | |
|---|---|---|---|
| 3,464,876 A | 9/1969 | Gerson | |
| 5,458,590 A | 10/1995 | Schleinz et al. | |

(Continued)

FOREIGN PATENT DOCUMENTS

| | | |
|---|---|---|
| DE | 36 40 979 A1 | 8/1987 |
| DE | 100 43 217 A1 | 3/2002 |

(Continued)

OTHER PUBLICATIONS

Webster's New Dictionary, p. 459, 1984 (month unknown).

(Continued)

*Primary Examiner* — Robert Vetere
*Assistant Examiner* — Lisha Jiang
(74) *Attorney, Agent, or Firm* — Buchanan Ingersoll & Rooney PC (57) ABSTRACT

A patterned layer is intended to be used in an absorbent article, and has a pattern, for example in the form of a text or an image, which appears clearly legible or interpretable for an observer at a certain distance. The pattern can be formed by a number of dots which, when the layer is in a first state, have a first surface density which forms the legible or interpretable pattern and which, when the layer is in a second and then expanded state, have a second surface density which is lower than the first surface density in the first state, the pattern becoming in the second state essentially illegible or uninterpretable for the observer at the given distance on account of the lower surface density.

13 Claims, 5 Drawing Sheets

(56) References Cited

U.S. PATENT DOCUMENTS

| | | |
|---|---|---|
| 2001/0018579 A1* | 8/2001 | Klemp ................... 604/385.25 |
| 2001/0047160 A1 | 11/2001 | Klemp |
| 2002/0052439 A1* | 5/2002 | Farooq ........................ 524/437 |
| 2003/0114826 A1* | 6/2003 | Roessler et al. ......... 604/385.28 |
| 2004/0055482 A1* | 3/2004 | Grounds et al. ................ 101/35 |
| 2004/0058130 A1 | 3/2004 | Nissing |
| 2006/0068168 A1 | 3/2006 | Olson et al. |

FOREIGN PATENT DOCUMENTS

| | | |
|---|---|---|
| EP | 0876809 A1 | 11/1998 |
| EP | 1175922 A2 | 1/2002 |
| GB | 2360250 A | 9/2001 |
| JP | 3-090602 A | 4/1991 |
| WO | WO 94/12133 A1 | 6/1994 |
| WO | WO 96/19351 A1 | 6/1996 |
| WO | WO/02/27098 * | 4/2002 |
| WO | WO 2004/057110 A1 | 7/2004 |

OTHER PUBLICATIONS

European Examination Report issued in corresponding European patent Application No. 04809134.2, dated Apr. 27, 2010.

* cited by examiner

METHOD OF MAKING A PATTERNED LAYER FOR ABSORBENT ARTICLE

CROSS-REFERENCE TO RELATED APPLICATION

The present application is a continuation of U.S. Ser. No. 11/017,659, filed on Dec. 22, 2004 (now abandoned), which claims the benefit of U.S. Provisional Application Ser. No. 60/531,037, filed on Dec. 22, 2003. The entire contents of U.S. Ser. No. 11/017,659 (now abandoned) and U.S. Provisional Application Ser. No. 60/531,037 are incorporated herein by reference.

TECHNICAL FIELD

The invention relates to a method for making a patterned layer intended to be used in an absorbent article, having a pattern, for example in the form of a text or an image, which appears legible or interpretable for an observer at a certain distance.

BACKGROUND

In absorbent articles such as diapers, sanitary towels, incontinence pads etc., it is known to apply texts and/or patterns to certain layers included in the article. The texts are preferably of an informative nature, for example in the form of user instructions or a warning text. The pattern is preferably in the form of a decorative pattern and/or in the form of a handling example. The texts and the pattern are usually arranged on one of the layers which form the outside of the article, for example on the front panel, the rear panel or one of the side panels which extend between the front panel and the rear panel. So as to be read and observed by the user before the article is used, the texts and patterns consist of a continuous dyed pattern. When the article is used, on the other hand, it is not desirable for either the text or the pattern to remain because the text or the pattern may then show through the article of clothing the user has on, which may be regarded as indiscreet and therefore unattractive by the user.

In order to avoid the problem mentioned above, it is known for the text and/or the pattern to be arranged on a separate layer which is attached detachably to the article. Before use, the user reads the text or looks at the image/the pattern and then removes the separate layer. It is true that the text/the pattern disappears as a result of this procedure, but a problem remains, namely that the separate layer which has now been removed has formed a residual product which has to be dealt with. The user should then either find a suitable place to dispose of the separate layer or, if no such place is to be found, retain the separate layer until such a place is found.

OBJECT AND SUMMARY

There is therefore a requirement for an improved absorbent article where the user can make out a pattern on the article before use and where the pattern essentially disappears when the article is used without the user having to perform any special action in order to achieve this.

A preferred embodiment aims to solve the problems indicated above. The problem is solved by a patterned layer intended to be used in an absorbent article, where the layer has a pattern, for example in the form of a text or an image, which appears clearly legible or interpretable for an observer at a certain distance.

An embodiment is characterized in that the pattern is formed by a number of dots which, when the layer is in a first state, have a first surface density which forms the legible or interpretable pattern and which, when the layer is in a second and then expanded state, have a second surface density which is lower than the first surface density in the first state, the pattern becoming in the second state essentially illegible or uninterpretable for the observer at the given distance on account of the lower surface density.

The pattern can consist of one or more groups of separate dots, where, for example, a first group forms a pattern in the form of one or more letters and where a second group forms a pattern in the form of a colored band or logotype or the like.

One advantage of the embodiment is that the pattern is clearly visible for a user in the first state and that the pattern becomes faint and diffuse in the second state. The pattern can consist of, for example, a certain color which indicates the absorption capacity of the article. The pattern can moreover consist of a text message, for example in the form of one or more letters which indicate, for example, the size of the article. It is preferable for the pattern to be clear in the first state as otherwise the user may make a mistake and in this way obtain an article of the wrong size or absorption capacity. When the user puts the article on, on the other hand, it is desirable from the point of view of the user that the pattern disappears or at least takes on a slightly more neutral appearance as otherwise there is a risk that the pattern will be visible through the clothes of the user. One of the major advantages of the embodiment therefore resides in the fact that, when the layer is expanded from the first state into the second state, the pattern is broken up and becomes faint and diffuse, which results in a reduced risk of the pattern showing through garments lying outside. "Broken up" means that the pattern is disintegrated or otherwise reduces its surface density in such a way that the pattern becomes fainter and more diffuse in the second state than in the first state.

Another advantage is that the present embodiment does not result in any such residual product as is obtained in the previously known art when a detachable strip is removed in order to eliminate the pattern when the article is used. Further examples of advantages are that the pattern can consist of an instruction text or an image series which indicates how the article is to be folded together after use. The pattern is then broken up, faint and diffuse during use, that is to say in the second state, but becomes visible when the user takes the article off as the article contracts into the first state, the pattern then becoming visible. It should be mentioned here that at least the layer which bears the pattern is preferably elastic or comprises elastic means/components which allow the elastic deformation from the first state into the second state and also the return from the second state into the first state. The elastic means can consist of, for example, elastic threads or elastic strips. The layer is therefore drawn together in the first state on account of the elastic means and extended in the second state by a force applied to the layer.

According to an embodiment, the layer is preferably puckered in the first state in such a way that the layer forms elevations and depressions, where the layer is in the main smoothed out in the second state. Here, the pattern can be formed by dye being applied to the elevations on one side of the layer in such a way that the first surface density is obtained. The dye can be applied by, for example, dye being sprayed onto the layer when the layer is in the first state.

One advantage of this embodiment is that the dyed elevations consist of small specks or dots which in the first state come together to form larger spots which in turn come together to form the desired pattern. "Come together" means here and below that the dots have such high surface density in the first state that the pattern formed by the dots is clearly interpretable for a user at a certain distance. The pattern is preferably clear that it has a signal function, that is to say it provides an indication which is obvious for the user of what the pattern is intended to show.

In another embodiment, the dots are arranged on the layer when the layer is in an expanded state which exceeds or is the same as the expanded second state. The dots are then applied to the layer in the expanded state with a surface density which is lower than or the same as the surface density in the second state.

In another embodiment, the dots are applied in the first state to a plane expandable material which in the second state is expanded in such a way that the dots are broken down into smaller component parts and/or that the mutual spacing of the dots is increased so that the surface density decreases to such a level that the pattern becomes broken up and thus faint and/or diffuse in the second state.

The pattern can consist of a dye which dyes the layer in a desired way. The pattern then preferably has a surface density in the first state which gives a first color strength which can be perceived by the user as interpretable and a surface density in the second state which is perceived by the user as a fainter and weaker color strength.

According to one embodiment, the layer can consist of two layers which have been joined together at points. The separate dots which form the pattern can then consist of bonding points which are at least partly dyed. PCT SE03/01959 indicates an advantageous method of interconnecting two layers by forming bonding points at the same time as dyeing of at least parts of the bonding points takes place. Here, the separate dots are brought about by selected parts of a stamping device, for example a stamping roller, being dye-coated in such a way that the dye-coated parts give rise to the dyed separate dots. The selected parts mean a number of the three-dimensional raised portions of the stamping device which are intended to form a three-dimensional stamped pattern in the layer. Those parts of the raised portions which are dye-coated are the tops of the three-dimensional raised portions. The bonding points are formed by a device acting against the dye-coated tops in such a way that the bonding points arise in the layer between the tops and the device at the same time as at least parts of the bonding points are dyed. The tops can moreover comprise raised microportions which are dye-coated. The dye-coated raised microportions subsequently form the at least partly dyed bonding points.

The bonding points according to PCT SE03/01959 preferably consist of a melt brought about by using an ultrasound device or a counterpressure roller which acts against the dye-coated tops and, where appropriate, the raised microportions. The method according to PCT SE03/01959 can also be used for dyeing an individual layer at points. The stamping device then produces a three-dimensional stamped pattern which is at least partly dyed. A great advantage of the method is that the simultaneous dyeing and stamping/joining together produces distinct and clearly dyed dots.

An example of how a layer can be dyed at points in order to achieve the effect proposed according to the invention is described below. The dots have a size of roughly 0.05-3.0 mm, preferably 0.1-2.0 mm, and most preferably 0.15-1.0 mm. The dots are moreover preferably designed as round spots but can of course be designed with any geometry, for example oval, rhombic, square, rectangular or any other shape suitable for the purpose, or combinations of different geometries. The surface density of the pattern in the second state is 10-300 dots/cm$^2$, preferably 20-200 dots/cm$^2$, and most preferably 30-150 dots/cm$^2$.

Preferred embodiments are not limited to the parameters indicated in the example but depends on inter alia how the layer is dyed, the dye used, the material of which the layer consists etc. As an example, it may be mentioned that a strongly coloring dye results in fewer dots of smaller size being necessary than if a less strongly coloring dye is used. Another example is if the layer itself is colored, which results in special requirements for the size of the dots, coloration and number in order that the pattern will in the first state be a legible/interpretable pattern for an observer at a certain distance and in the second state become a broken-up and thus diffuse pattern.

It may also be mentioned here that the distance mentioned above preferably means a normal reading distance, that is to say that the layer lies within an arm's length of the observer. It should also be mentioned, however, that a distance exceeding an arm's length may also be relevant. As an example, the situation when the pattern is intended to attract a potential purchaser/user may be mentioned, for example when a product is located on a shelf or the like, where the distance may then be of the order of a few meters. However, it is preferred that the observer be able to perceive the pattern as legible/interpretable when the layer is in the first state and illegible/uninterpretable when the layer is in the second state. The surface density of the dots is therefore preferably sufficiently high in the first state that a user at the distance desired (by the manufacturer) will perceive a specific pattern intended to give the observer certain information or a certain signal.

As the pattern is preferably made up of separate dots, however, the observer may at too close a distance perceive the pattern in the first state as diffuse because the pattern will then to the perception of the observer be broken up into the separate dots. The distance is therefore significant for the observer perceiving that the dots come together to form the pattern intended by the manufacturer. In the manufacture of the article, account should therefore preferably be taken of all the parameters mentioned above in order to obtain the desired effect of the embodiment, namely an interpretable pattern in a first state of the layer and an uninterpretable and diffuse pattern in a second and then expanded state.

DESCRIPTION OF THE FIGURES

Preferred embodiments will be described below in connection with a number of figures in which.

PREFERRED EMBODIMENTS

In all the embodiments described below, X2 indicates a distance which is greater than X1, and Y2 a distance which is greater than Y1.

Figure 1:
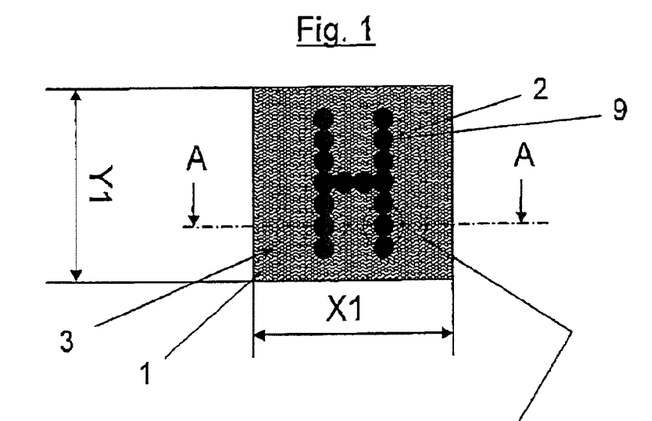
FIG. 1 shows diagrammatically a first embodiment where a patterned layer is in a first state.

FIG. 1 shows a first embodiment where a patterned layer 1 with a length X1 (X direction) and a width Y1 (Y direction) is in a first state. Here, the pattern consists of a number of separate black dots 9 which together form the letter H. In FIG. 1, the layer 1 is in a drawn-together state where the layer 1 has puckered. FIG. 1 therefore shows the layer 1 in a puckered first state. The fact of the layer being puckered is marked in FIG. 1 by a wave-shaped pattern 3. The layer can be puckered in the X direction, the Y direction or both the X direction and the Y direction. The puckered layer 1 comprises elevations and depressions therebetween. In FIG. 1, the dots 9 have been formed by dye having been applied at points to the layer in such a way that a number of the wave-shaped elevations have been dyed when the layer 1 is in the puckered state. This will be explained in greater detail in connection with FIG. 2.

Figure 2:
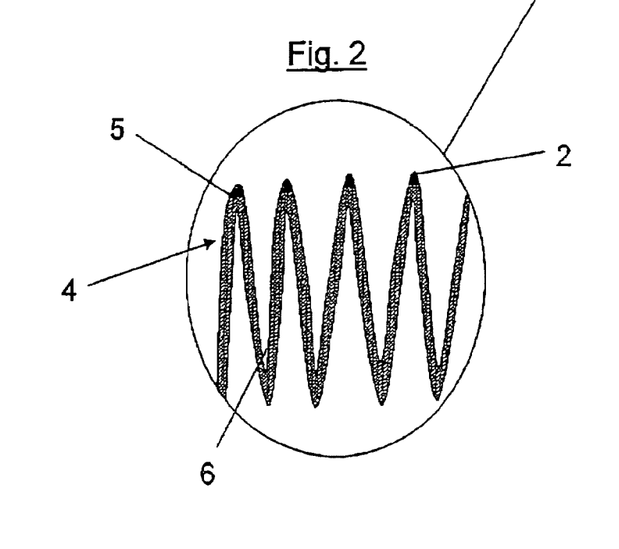
FIG. 2 shows diagrammatically an enlarged portion of a part of the layer according to FIG. 1 seen in the cross section A-A in FIG. 1.

FIG. 2 shows an enlarged portion of a part of the layer 1 according to FIG. 1 seen in the cross section A-A in FIG. 1. FIG. 2 shows that the dye has been applied to the tops 5 of the elevations 4 on one side of the layer. The dyed tops 5 constitute the actual microdots 2 which in the first state together form the dots 9 which in turn form the pattern H. In FIG. 2, it can be seen that the depressions 6 have not been dyed. The dyeing of the elevations 4 can be carried out by, for example, dye being sprayed onto the elevations 4 when the layer 1 is in the first state.

Figure 3:
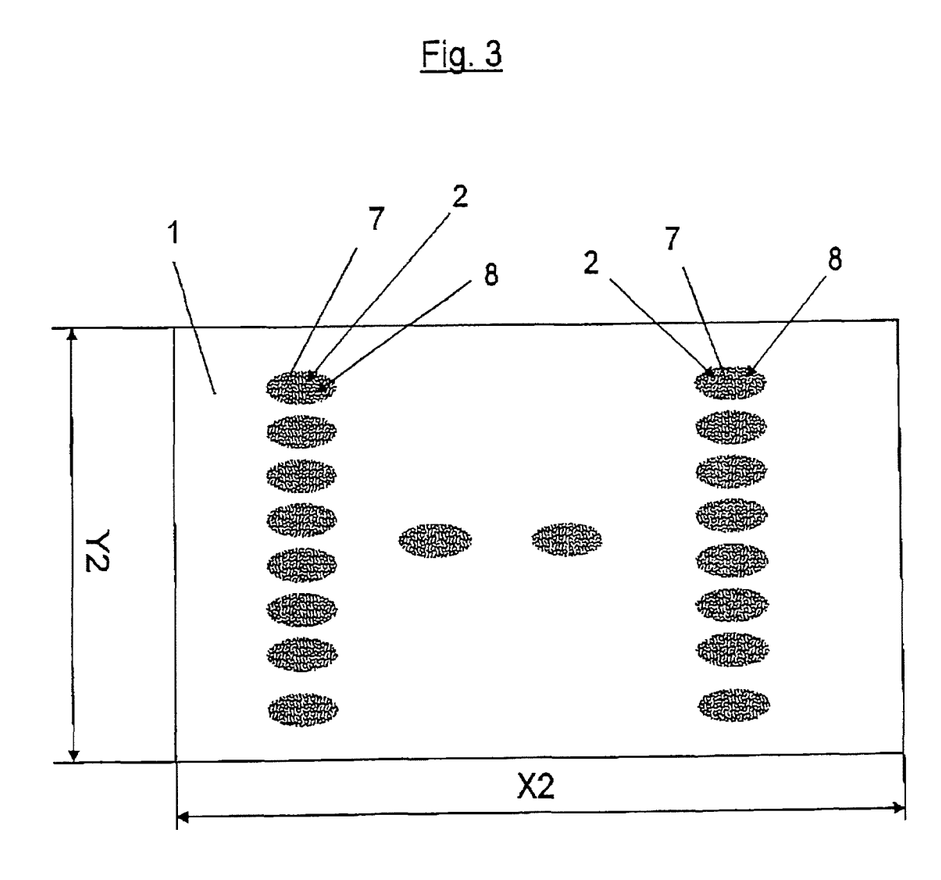
FIG. 3 shows diagrammatically the layer according to FIGS. 1 and 2 where the layer has been expanded into a second state.

FIG. 3 shows the layer 1 according to FIGS. 1 and 2 where the layer 1 has been expanded into a second state with a length X2 and a width Y2, where X2 is greater than X1 and where Y2 is greater than Y1. FIG. 3 shows that the layer 1 is in a smoothed-out state, that is to say where the puckered parts in FIG. 1 are smoothed out, which has given rise to the dots 9 having been broken up into a diffuse pattern which could be interpreted as an unclear and diffuse H where the dots 9 have been broken up into a number of separate grey spots 7 with a mutual spacing between them. The spots 7 too are diffuse owing to the fact that the spots 7 consist of a number of black dots 8 which originally constituted the dyed tops 5, that is to say the microdots.

FIG. 3 shows that the spots 7 are oval with an extension in the X direction. The spots 7 are oval because the layer has been expanded more in the X direction than in the Y direction. The pattern H is therefore broken up in a number of ways by virtue of the layer 1 having been expanded by different amounts in different directions, but, irrespective of how the layer 1 is expanded, a breaking-up of the pattern H can take place in such a way that the pattern H shown in FIG. 1 becomes more diffuse for an observer in the second state shown in FIG. 3.

As can be seen from FIG. 3, the diffuse pattern is in the second state perceived by an observer as grey spots 7 with a spacing between the spots 7. In FIG. 1 on the other hand, the layer 1 is in the drawn-together first state, the dyed tops 5 being located at a mutual spacing which results in an observer, at the same distance as the observer of FIG. 3, perceiving that the dyed tops 5, that is to say the microdots 2, come together to form the black dots 9 which in turn come together in such a way that the H-shaped pattern appears. This rationale leads to the pattern, that is to say the dyed tops 5 (the microdots 2) and therefore also the black dots 9, having a higher surface density in the first state than in the second state.

Figure 4:
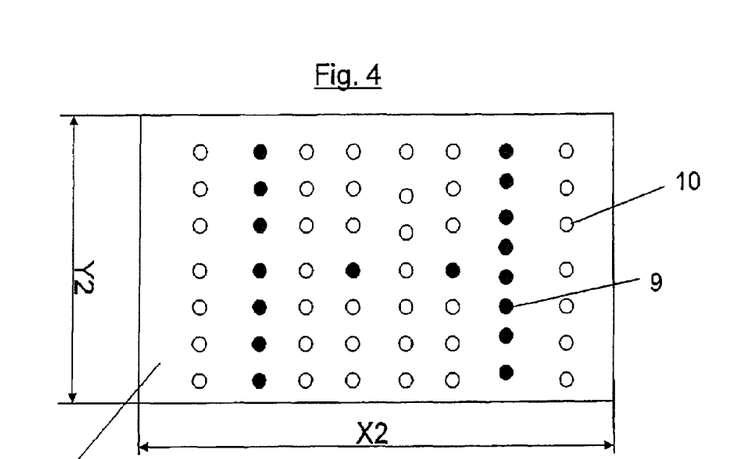
FIG. 4 shows diagrammatically a second embodiment where the dye is applied at points to a layer which is in the second state.

FIG. 4 shows a second embodiment where the dye is applied at points to a layer 1 which is in the second state, that is to say in an expanded state where the layer has the length X2 and the width Y2. The dye is applied in the form of separate dots 9. In the second state, the dots 9 are located at such a spacing from one another than the pattern H is perceived by an observer as diffuse and unclear. FIG. 4 shows moreover that the layer has been stamped with impressions 10 in the form of a punctiform pattern, where only a number of the punctiform impressions 10 have been dyed to form the dots 9. The punctiform impressions 10 can constitute a three-dimensional pattern in a layer but can also constitute bonding points between two layers. The punctiform impressions 10 can be brought about by, for example, one or more layers being guided between a stamping roller and an opposite ultrasound device or an opposite counterstay roller. PCT SE03/01959 indicates an advantageous method of interconnecting two layers by forming bonding points at the same time as dyeing of at least parts of the bonding points takes place. Here, the separate dots are brought about by selected parts of the stamping roller being dye-coated in such a way that the dye-coated parts give rise to the dyed separate dots 9.

Figure 5:
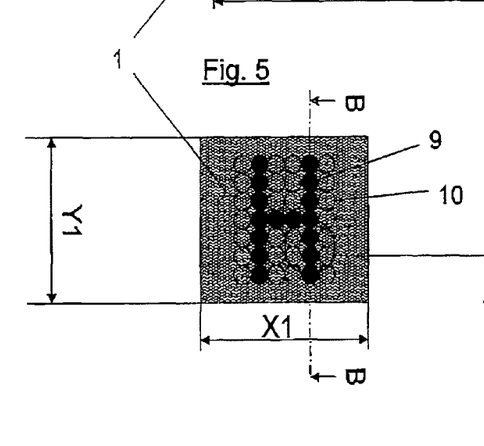
FIG. 5 shows diagrammatically the layer according to FIG. 4 in the first state.

FIG. 5 shows the layer 1 according to FIG. 4 in the first state, that is to say when the layer is contracted to the length X1 and the width Y1. FIG. 5 shows by means of a wave pattern that the layer is puckered with elevations and depressions in the first state.

Figure 6:
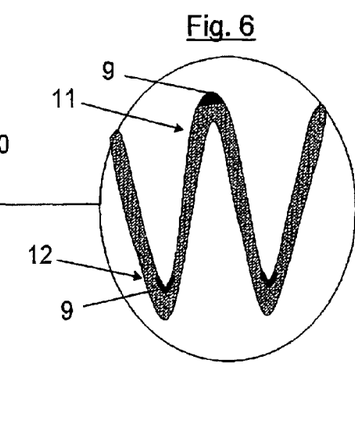
FIG. 6 shows diagrammatically an enlarged portion of a part of FIG. 5 in the section B-B.

FIG. 6 shows an enlarged portion of a part of FIG. 5 in the section B-B where the dots 9 are located both on the elevations 11 and in the depressions 12. This means that the pattern H in FIG. 5 appears clearly for an observer when the layer is in the drawn-together first state on account of the spacing between the dots 9 being so small that, for an observer, the dots come together to form the pattern H. Here, the first state can mean a state of the layer when both the dyed elevations 11 and the dyed depressions 12 are visible in such a way that, for the observer, the dots 9 come together sufficiently for the pattern H in FIG. 5 to be clearly visible.

In the second embodiment described in connection with FIGS. 4-6, the pattern, that is to say the black dots 9, has a higher surface density in the first state than in the second state, which produces the desired effect with a clearly visible pattern in the first state and where the pattern has been broken up into a faint and diffuse pattern in the second state.

Figure 7:
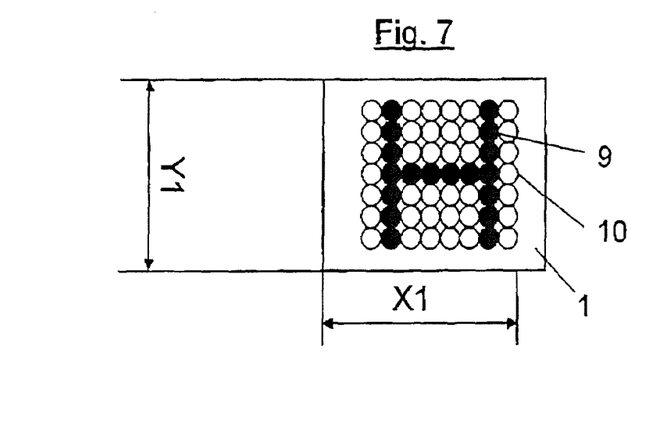
FIG. 7 shows diagrammatically a third embodiment where the dye is applied at points to a plane or smooth layer 1 which is in the first state.

FIG. 7 shows a third embodiment where the dye is applied at points to a plane or smooth layer 1 which is in the first state, that is to say in a contracted state where the layer 1 has the length X1 and the width Y1. The dye is applied in the form of separate dots 9. In the first state, the pattern H appears clearly for an observer on account of the fact that the spacing between the dots 9 is so small that, for an observer, the dots come together to form the pattern H. FIG. 7 shows that the layer 1, like the layer in FIG. 4, has been stamped with impressions 10 in the form of a punctiform pattern, where only a number of the punctiform impressions 10 have been dyed. Here too, the punctiform impressions 10 can constitute a three-dimensional pattern in a layer but can also constitute bonding points between two layers.

Figure 8:
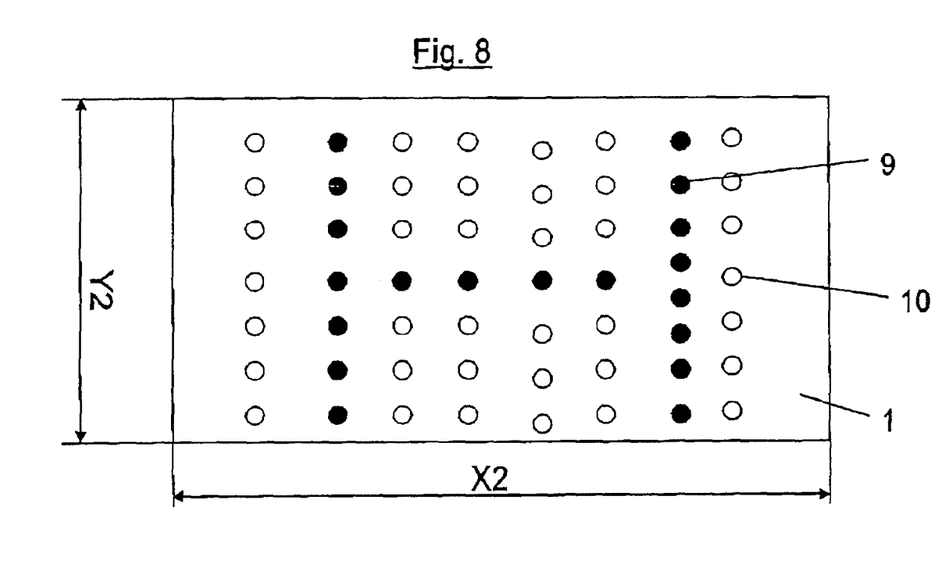
FIG. 8 shows diagrammatically a layer according to FIG. 7 in the second state.

FIG. 8 shows a layer 1 according to FIG. 7 in the second state, that is to say when the layer has the length X2 and the width Y2. In the second state, the dots 9 are located at such a spacing from one another that the pattern H is perceived by an observer as diffuse and unclear.

In the third embodiment described in connection with FIGS. 7 and 8, the pattern, that is to say the black dots 9, has a higher surface density in the first state than in the second state, which produces the desired effect with a clearly visible pattern in the first state and where the pattern has been broken up into a faint and diffuse pattern in the second state. In the second state, it has been possible for the dots to be disintegrated and therefore for the pattern to be broken up by the points having been disintegrated. An alternative is when the dots constitute bonding points which are not expandable. When the layer is expanded from the first state into the second state, the dots do not therefore expand, but only the material between the dots expands, which gives rise to the increased spacing between the dots 9 in the second state.

Figure 9:
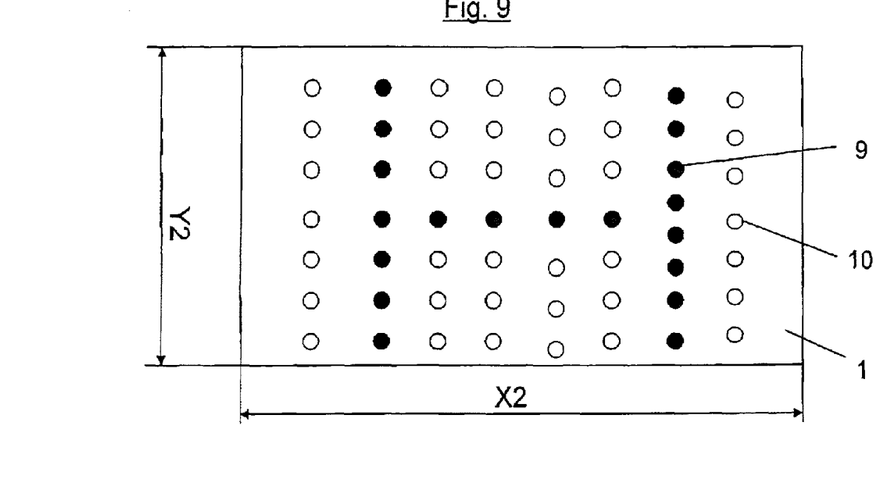
FIG. 9 shows diagrammatically a fourth embodiment where the dye is applied at points to a plane or smooth layer which is in the second state.

FIG. 9 shows a fourth embodiment of the invention where the dye is applied at points to a plane or smooth layer 1 which is in the second state, that is to say in an expanded state where the layer has the length X2 and the width Y2. The dye is applied in the form of separate dots 9. In the second state, the dots 9 are located at such a spacing from one another that the pattern H is perceived by an observer as diffuse and unclear. FIG. 9 shows, like in FIGS. 4 and 7, that the layer has been stamped with impressions 10 in the form of a punctiform pattern, where only a number of the punctiform impressions have been dyed.

Figure 10:
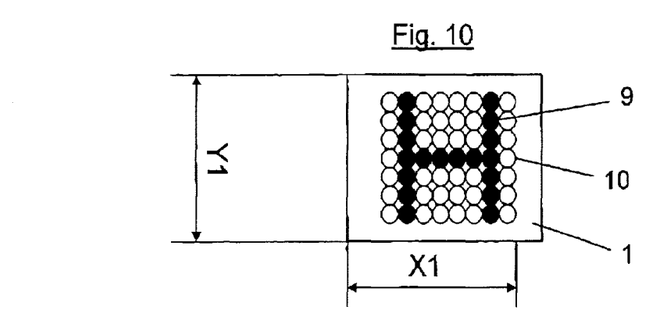
FIG. 10 shows diagrammatically a layer according to FIG. 9 in the first state.

FIG. 10 shows a layer 1 according to FIG. 9 in the first state, that is to say when the layer has the length X1 and the width Y1. In the first state, the pattern H appears clearly for an observer on account of the fact that the spacing between the dots 9 is so small that, for an observer, the dots come together to form the pattern H.

In the fourth embodiment described in connection with FIGS. 8 and 9, the pattern, that is to say the black dots 9, has a higher surface density in the first state than in the second state, which produces the desired effect with a clearly visible pattern in the first state and where the pattern has been broken up into a faint and diffuse pattern in the second state.

The stamping indicated in FIGS. 4-10 can be replaced by only punctiform dyeing of the layer, the same result in terms of the clarity of the pattern H in the first state and the second state being achieved as discussed above in connection with FIGS. 4-10.

In all the embodiments, the layer may advantageously consists of an elastic material or of an inelastic material comprising elastic means, for example elastic bands or threads.

It is however understood that the article described above and shown in the drawings only represents a non-limiting example and that the present invention is not limited thereto, but can be used in any type of absorbent articles as defined above.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A method for producing a patterned layer of material for an absorbent article, the patterned layer of material having a puckered first state including elevations and depressions when no tension is applied to the patterned layer, and having a second and expanded state in which the patterned layer of material is at least partly smooth when tension is applied to the patterned layer, the method comprising:
    gathering a layer of material Into the puckered first state including elevations and depressions;
    applying a color to the layer of material while the layer of material is gathered in the first state such that the color is applied only to the elevations of the layer of material to create a pattern in the form of a text or an image on the gathered layer of material, which pattern appears legible or interpretable for an observer at a certain distance when the layer of material is in the puckered first state;
    the color including a number of dots being arranged on the elevations so that when the layer of material is in the first state, the dots together have a first surface density which forms the legible or interpretable pattern; and
    when the layer of material is in the second and expanded state, the dots together have a second surface density which is lower than the first surface density in the first state, the pattern being essentially illegible or uninterpretable for the observer at the given distance on account of the second lower surface density when the layer is in the second state.

2. The method according to claim 1, wherein the color is formed with a dye.

3. The method according to claim 1, applying an elastic material to the layer of material to gather the layer of material together in the first state.

4. The method according to claim 1, wherein the layer of material is elastic.

5. The method according to claim 1, wherein the pattern has a first color strength in the first state and fainter and weaker color strength in the second state.

6. A method for producing a patterned layer of material for an absorbent article, the method comprising:
    providing a layer of material having a puckered first state including elevations and depressions, and a second and expanded state in which the layer of material is at least partly smooth;
    applying a number of isolated dots to the layer of material to create a pattern in the form of a text or an image on the layer of material, which pattern appears legible or interpretable for an observer at a given distance when the layer of material is in the puckered first state;
    the number of dots being arranged to come together in the puckered first state to form spots which in turn come together to form the pattern, each of the spots comprising a plurality of the dots; and
    when the layer of material is in the second and expanded state, the dots are separated so that the spots forming the pattern are broken up and the pattern becomes faint, diffuse, and essentially illegible or uninterpretable for the observer at the given distance.

7. The method according to claim 6, wherein the layer of material is elastic.

8. The method according to claim 6, wherein the pattern is colored and has a first color strength in the first state and fainter and weaker color strength in the second state.

9. The method according to claim 6, wherein the spots forming the pattern are applied only to the elevations.

10. A method for producing a patterned layer of material for an absorbent article, the method comprising:
    forming a plurality of punctiform impressions in a layer of material;
    forming the layer of material to have a first state including elevations and depressions, and to have a second state in which the layer of material is at least partly smooth;
    dying at least some of the punctiform impressions to create the pattern in the form of a text or an image, which pattern appears legible or interpretable for an observer at a certain distance when the layer of material is in a first state, and which is essentially illegible or uninterpretable for the observer at the given distance in a second state of the layer of material;

wherein at least some of the plurality of punctiform impressions are formed at the elevations, and only the punctiform impressions at the elevations are dyed.

11. The method according to claim 10, wherein the dying step is performed when the layer of material is in the second state.

12. The method according to claim 10, wherein the punctiform impressions are three dimensional.

13. The method according to claim 10, wherein the punctiform impressions comprise bonding points between the layer of material and another layer of the absorbent article.

* * * * *